United States Patent [19]
Carlsson et al.

[11] Patent Number: 5,125,841
[45] Date of Patent: Jun. 30, 1992

[54] IMPRESSION TOP

[75] Inventors: Lennart Carlsson; Lars Jörnéus, both of Mölndal, Sweden

[73] Assignee: Nobelpharma AB, Goteborg, Sweden

[21] Appl. No.: 641,677

[22] Filed: Jan. 16, 1991

[30] Foreign Application Priority Data

Jan. 18, 1990 [SE] Sweden .................. 9000175

[51] Int. Cl.⁵ .......... A61C 5/08; A61C 13/12; A61C 13/225
[52] U.S. Cl. .................. 433/213; 433/172; 433/214
[58] Field of Search .............. 433/172, 174, 177, 213, 433/214, 173

[56] References Cited

U.S. PATENT DOCUMENTS

| | | | |
|---|---|---|---|
| 3,932,939 | 1/1976 | Weissman | 433/213 |
| 4,571,186 | 2/1986 | Pipko | 433/181 |
| 4,708,654 | 11/1987 | Branemark | 433/213 |
| 4,955,811 | 9/1990 | Lazzara et al. | 433/173 |
| 5,007,833 | 5/1991 | Barbone | 433/172 |
| 5,052,928 | 10/1991 | Andersson | 433/172 |
| 5,055,047 | 10/1991 | Names | 433/214 |

FOREIGN PATENT DOCUMENTS

| | | |
|---|---|---|
| 3110694 | 9/1982 | Fed. Rep. of Germany. |
| 3807591 | 9/1989 | Fed. Rep. of Germany ...... 433/213 |
| 9001909 | 3/1990 | PCT Int'l Appl. . |

Primary Examiner—Cary E. O'Connor
Assistant Examiner—Cindy A. Cherichetti
Attorney, Agent, or Firm—Pollock, Vande Sande & Priddy

[57] ABSTRACT

A device for transferring the direction and position of a dental implant or its extension element, such as a spacer element, to a work model, includes a base part and an elongate upper part projecting from the base part. The device is made of an elastic material so that clamp fitting is obtained between the base part and the implant or its extension element. The upper part has a geometry which provides for retention in the surrounding impression compound and has break notches so that it can easily be shortened.

5 Claims, 1 Drawing Sheet

IMPRESSION TOP

FIELD OF THE INVENTION

The present invention relates to a device for transferring the position and direction of a dental implant or its extension element, that is the spacer element, to a so-called work model.

BACKGROUND OF THE INVENTION

It is already known to permanently anchor. a dental prosthesis in the jaw with the aid of titanium screws implanted in the jawbone. The screws are anchored in holes in the bone so that the upper part of the screw is situated level with or directly below the upper surface of the jawbone. The screw is then covered over with a flap of mucous membrane and is left unloaded for a rest period of 3 to 6 months in order for the bone to grow firmly to and form a unit with the implanted screw. After the rest period, the screw is exposed and a spacer element, preferably also of titanium, is arranged on the screw, after which a dental prosthesis is anchored on the spacer element. In this respect the dental prosthesis must be accurately adapted to the actual appearance of the jaw with the implanted titanium elements.

During the adaptation the dental technician works with a positive model of the patient's jaw, which model has been produced by taking a negative impression of the jaw with the aid of an impression spoon filled with impression compound. The hardened impression is then removed from the jaw and is filled with cast compound which is allowed to harden, a positive cast of the patient's jaw being obtained with projecting columns corresponding to the spacer elements of the implants projecting above the arch of the palate.

Swedish Patent 446,371 describes a method for facilitating the production of a model of the abovementioned type.

The position of the spacer elements is transferred to the impression with the aid of so-called guide elements (impression tops). These guide elements have a part which cooperates with the connection surface of the spacer element and a part for fixation in the impression material. The guide elements are secured on the spacer elements with guide pins (long screws). When the impression compound has hardened. the guide pins are unscrewed and the impression with the guide elements now set in is removed from the patient's mouth. Dummies of a geometry similar to that of the spacer elements are then screwed securely to the impression tops, and the impression is filled with modelling compound, usually plaster. When the plaster has hardened, the guide pins are unscrewed, and the impression with the guide elements is removed. A positive work model with molded-in dummies has now been obtained.

The method described in the above swedish patent can be used in cases where the spacer element comprises an internal thread in which the guide pin can be screwed down. However, other types of spacer elements which do not have an internal thread have recently been developed. Particularly in so-called single-tooth replacements, a type of spacer element is used whose base, in a similar manner to earlier spacer elements, is adapted to the upper part of the fixture and which has an upper, elongate narrower part of hexagonal design. There is no internal thread, and the impression top cannot therefore be secured with the aid of a guide pin.

SUMMARY OF THE INVENTION

An object of the invention is to provide a device (impression top) which facilitates the present production of a work model and which can be used also for the abovementioned type of spacer element. Another object of the invention is to simplify the method so as to avoid the laborious process of screwing the impression top securely to the spacer element and the dummy. This is achieved by and adapting the clamping force between the impression top and the spacer element such that the impression top sits so securely that it does not fall off, but not so hard that it is drawn out of the hardened impression compound. It is desirable to have a greater clamping force between the impression top and the dummy than that between the impression top and the spacer element. This is due to the fact that, when producing the model, the plaster is normally vibrated together. In this process no plaster is allowed to penetrate between the dummy and the impression top. If this happens, the dummy takes up the wrong position, and the accuracy is completely lost.

This has been solved by means of the fact that the device is made of an elastic material so that clamp fitting is obtained between the base part of the device and the implant or its extension element.

In an advantageous embodiment the device is provided with an upper part which has a geometry which provides for retention in the surrounding impression compound and which has break notches so that it can be easily shortened.

One embodiment of the present invention is shown diagrammatically in the accompanying drawings, in which:

BRIEF DESCRIPTION OF THE DRAWINGS

FIG. 3 shows a dummy for casting in a work model.

DETAILED DESCRIPTION OF THE PREFERRED EMBODIMENT

In the production of a work model it is important for the dummies to have the same orientation in the finished model as the spacer elements in the securing members implanted in the jawbone.

A negative impression is taken of the jaw with the spacer elements projecting over the arch of the palate. In this respect use is made of a dental impression spoon filled with soft impression compound, in the same manner as is described in the Swedish Patent 446,371.

Figure 2:
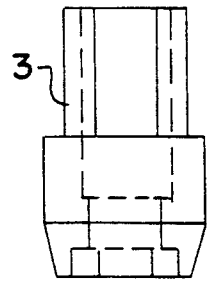
Figure 1C:
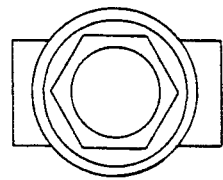
FIGS. 1A-1C show a device according to the present invention.
Figure 3A:
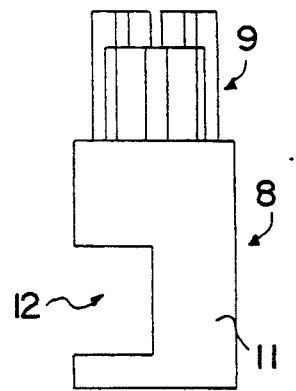
FIGS. 3A and 3B show the type of spacer element with which the present device is intended to cooperate.
Figures 1A, 1B:
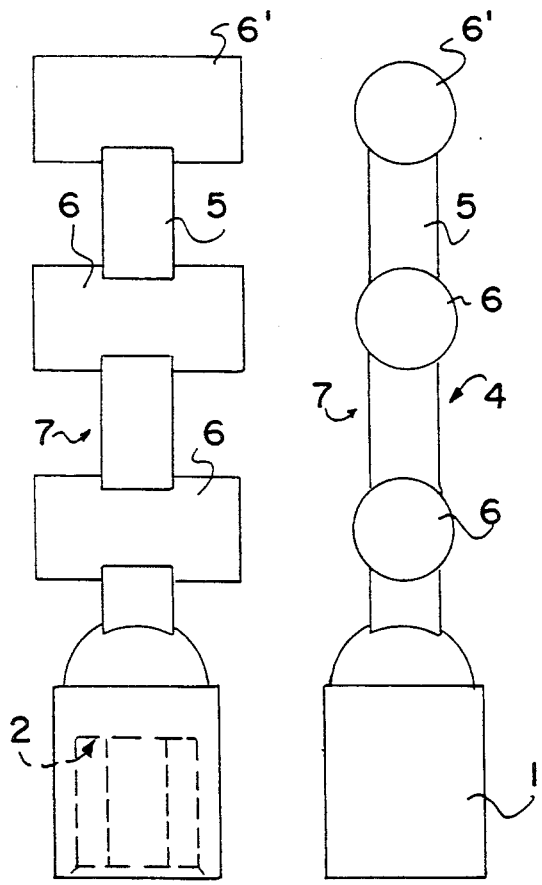
Figure 3B:
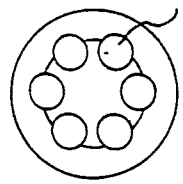

Before the impression spoon is arranged on the jaw, the spacer elements, which for example are designed in the manner shown in FIG. 2, are provided with an impression top whose base part 1 has a predetermined fitting to the spacer element. The base part is cylindrical with an internal hexagonal recess 2 which corresponds with accurate fitting to the hexagonal upper part 3 of the spacer element (FIG. 2).

Two cooperating hexagons can result in extremely large play in the rotational direction even in the case of a small diametrical play. In order to achieve the desired precision, preferably a complete absence of play, extremely accurate fitting is required. It could be achieved by means of extremely stringent precision requirements being imposed on the cooperating components, but such solution would be very costly.

According to the invention, the impression top is instead made of an elastic material, for example plastic, so that a clamp fitting is obtained between the base part of the device and the implant or its extension element, that is, a connection completely free from play.

The impression top moreover comprises an upper part with a geometry which provides for retention in the surrounding impression compound. The upper part 4 consists of a central, elongate beam 5 provided with a number of transverse rods 6, three in number being shown in the figure. The entire upper part is cast in one piece together with the base part 1 in the elastic material. The elongate beam 5 has a rectangular cross-section, while the transverse rods 6 have a circular cross-section with a diameter which slightly exceeds the width of the beam 5. The elongate beam 5 is terminated at the top with a transverse rod 6'. The transverse rods 6 counteract any unintentional turning of the impression top when it is set in the impression compound. The middle parts 7 between the transverse rods function both as prefabricated break notches for shortening of the impression top and as retention elements which prevent the position of the impression top from being altered in the axial direction after the impression compound has hardened.

A number of holes are normally made in the impression spoon so that the impression tops can project out through these when the impression spoon is applied on the jaw. In this way it is easy to establish that the impression top is in position during the period when the impression compound is hardening. If it is undesirable to make holes in the impression spoon, the impression top can be shortened by being broken or cut off. In this shortened state, the impression top is completely surrounded by impression compound.

The impression top is designed to cooperate with an elastically designed dummy 8 with an upper part 9 which comprises six rounded, projecting corners 10 and which corresponds to the hexagonal recess 2 in the base part of the impression top, and a cylindrical lower part 11 with a semicircular recess 12 for positive locking in the modelling compound. As a result of the elastically designed fitting, an extra high clamping force is obtained between the dummy and the impression top. The dummy can be made of the same plastic material as the impression top.

I claim:

1. A device for transferring the direction and position of a dental implant or its extension member to a work model, said device comprising:
   a unitary member including a cylindrical, wider base part having an internal hexagonal recess which is dimensioned for an accurate fitting onto a corresponding hexagonal upper part of the implant or its extension member;
   an upper part of said unitary member including an elongate member projecting upwardly from said base part, said upper part being designed to ensure retention of the device in a surrounding impression compound and being dimensioned to include a portion projecting beyond said impression compound;
   said upper part including a plurality of means for facilitating desired shortening of said upper part to eliminate said portion projecting beyond said impression compound;
   wherein said unitary member is made of an elastic material to ensure clamp fitting between said base part of said unitary member and the upper part of the implant or its extension member.

2. The device according to claim 1, wherein said upper part further includes a plurality of transverse rod-shaped elements spaced along said elongate member.

3. The device according to claim 2, wherein one of said transverse rod-shaped elements extends over t he top of said elongate member.

4. The device according to claim 3, wherein said means for facilitating shortening includes break notches.

5. The device according to claim 1, wherein said unitary member is adapted to cooperate with an elastic dummy such that an additional high damping force is obtained between said dummy and said base part of said unitary member.

* * * * *